United States Patent
Landgrebe et al.

[11] Patent Number: 5,827,325
[45] Date of Patent: Oct. 27, 1998

[54] IMPLANT IN PARTICULAR FOR THE TROCAR PUNCTURE POINTS

[75] Inventors: Susanne Landgrebe, Quickborn; Wieland Knopf, Georgenthal, both of Germany

[73] Assignee: Ethicon, Inc., Somerville, N.J.

[21] Appl. No.: 712,941

[22] Filed: Sep. 13, 1996

Related U.S. Application Data

[63] Continuation of Ser. No. 510,438, Aug. 2, 1995, abandoned, which is a continuation of Ser. No. 204,022, Feb. 28, 1994, abandoned.

[51] Int. Cl.⁶ .................................................. A61B 17/08
[52] U.S. Cl. ........................................... 606/213; 600/32
[58] Field of Search .................. 600/29–32; 128/897–9; 606/1, 213, 215; 623/1, 11; 604/15, 51, 60

[56] References Cited

U.S. PATENT DOCUMENTS

| 2,931,353 | 4/1960 | Kitzul | 600/32 |
| 3,447,533 | 6/1969 | Spicer | 600/32 |
| 4,209,009 | 6/1980 | Hennig | 600/32 |
| 4,890,612 | 1/1990 | Kensey | 606/213 |
| 5,108,421 | 4/1992 | Fowler | 606/213 |
| 5,312,435 | 5/1994 | Nash et al. | 604/15 |
| 5,342,393 | 8/1994 | Stack | 604/15 |

*Primary Examiner*—John P. Lacyk
*Attorney, Agent, or Firm*—Emil Richard Skula

[57] ABSTRACT

An implant, in particular for the closure of trocar puncture points, has a flexible, flat base part (1) and a stopper part (2) that starts from one side (3) of the base part (1) and extends in an essentially perpendicular manner relative to the base part (1). The stopper part (2) can be provided with a waist (5) in the vicinity of the base part (1).

11 Claims, 1 Drawing Sheet

IMPLANT IN PARTICULAR FOR THE TROCAR PUNCTURE POINTS

This is a continuation of application Ser. No. 08/510,438, filed Aug. 2, 1995 now ABN, which is a continuation of application Ser. No. 08/204,022, filed Feb. 28, 1994, now ABN.

TECHNICAL FIELD

The invention relates to an implant, in particular for the closure of trocar puncture points.

BACKGROUND OF THE INVENTION

In minimally invasive surgery, the operation instruments and observation instruments are introduced into the inside of the body through cannulae (trocar sleeves). The cannulae are previously introduced into the body wall using trocars. In the case of smaller cannulae diameters, roughly of the order of magnitude of 10 mm, injuries to the body wall are essentially punctiform, since the tissue yields around the puncture point without further tearing. As a rule, therefore, patients experience only slight stress from these injuries, which heal quickly following the operation.

It is the present trend to use cannulae with larger diameters in order also to be able to insert larger operation instruments, such as for example circular clip suture equipment, into the inside of the body. However, on inserting these larger cannulae, whose diameters are for example in the order of 30 mm, injuries are caused to the body wall which are not unproblematical. Thus, for example, on inserting such a cannula into the abdominal wall, injuries are caused, amongst others, to the external aponeurosis and the fascia transversalis, which play an essential part in stabilizing the abdominal wall. With such injuries there is basically the danger of later complications, such as a postoperative hernia. It can also lead to noticeable uloses which, for cosmetic reasons, are undesirable.

SUMMARY OF THE INVENTION

It is the object of the invention to provide a possibility of reducing the level of complications during the healing process of injuries, as are, for example, caused by the insertion of larger cannulae.

This object is achieved by an implant having the features of claim 1. Advantageous designs result from the dependent claims.

The implant according to the invention, in particular for the closure of trocar puncture points, has a flexible, flat base part and a stopper part that starts from one side of the base part and extends in an essentially perpendicular manner relative to the base. The stopper part is preferably cylinder-like and its free end face can be rounded. The general shape of the base part can be circular, and the stopper part can start from the middle zone of the base part. An implant designed in this way can easily be inserted into the trocar puncture point, as is explained in more detail below during the description of the embodiment. After insertion, the stopper part fills the actual puncture hole, pointing with the free end face to the inside of the body. The base part settles between the aponeurosis and the cutis if the implant is, for example, inserted into the abdominal wall. The stopper part is thus securely anchored with the help of the base part.

In a preferred version, the stopper part comprises a waist in the vicinity of the base part. The dimensions are preferably chosen so that, after the insertion of the implant, the waist lies in the area of the aponeurosis and the musculature, whilst the zone of the stopper part in the vicinity of its free end face protrudes slightly in the inside of the body. As the tissue tends to position itself against the implant following the insertion of the implant, the waist ensures an additional hold. The projecting section of the stopper part prevents the inner layers of tissue, such as for example the peritoneum, from growing uncontrolled into the zone of the penetration point, which would lead to an unwanted cicatrization.

The implant according to the invention enables the individual tissue layers of the body wall essentially to regenerate themselves again to regain their condition prior to the injury. This is because even slower-growing cells can gradually grow into the inside of the implant, without being displaced by fast-growing cells. The result is a structured formation of fresh tissue, and not an uncontrolled cicatrization which could lead to the possible complication of a cicatrix rupture (hernia). In order to permit the ingrowth of the cells into the inside of the implant or into the space taken up by the implant, the implant, or a section of it, can consist of porous material; a resorbable material can serve the same purpose, even if it is not porous.

When a new tissue structure which per se exhibits sufficient strength, has formed through the ingrowth of cell associations, the implant can be dispensed with. It therefore preferably consists of a resorbable material so that an unnecessary foreign body does not stay permanently in the tissue. In an alternative version, the base part could also be produced from non-resorbable material, in order to ensure an additional stability, permanently, i.e. after healing.

In a preferred version at least one thread is attached to the side of the base part facing away from the stopper part. The thread assists with the insertion of the implant as described below. Furthermore, the implant can be sewn with the help of the thread or threads to the outside body wall if the surgeon considers this necessary in order to fix the implant even more securely during the healing process. The thread material can be resorbable or non-resorbable. If non-resorbable material is used, the threads can be removed in the usual manner after some time, whereby their ends can be cut directly at the base part, so that no foreign body remains in the tissue.

The advantages of the implant according to the invention are, therefore, in summary, a simple and quickly performable wound closure, the avoidance of expensive plastics measures and the guarantee of a structured tissue build-up with safe cicatrization, so that no danger of a postoperative hernia exists. Finally, the use of the implant according to the invention also leads to satisfying results from a cosmetic point of view.

The invention is described in more detail below with reference to an embodiment:

DESCRIPTION OF THE PREFERRED EMBODIMENTS

Figure 1:
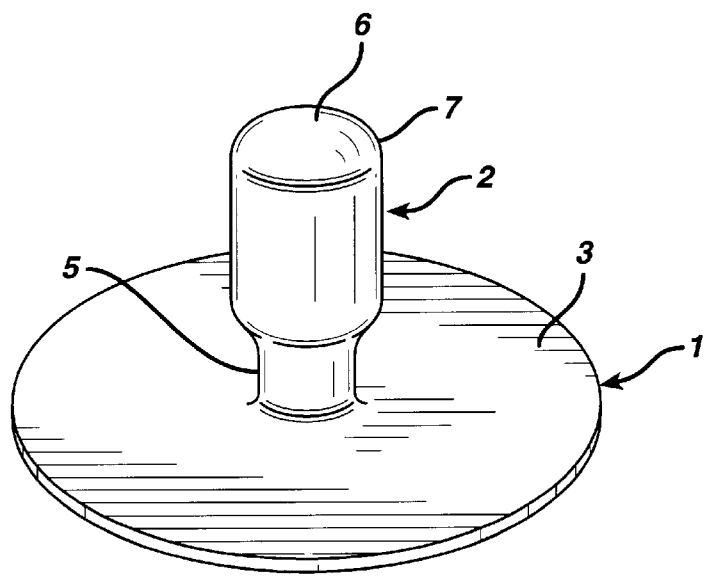
FIG. 1 a perspective view of an implant according to the invention.

As FIG. 1 shows, the implant has a base part 1 and a stopper part 2. The base part 1 is flat in design and consists of a flexible material. It can be woven or knitted or even consist of a film, e.g.

The stopper part 2 is cylinder-like and starts from the side 3 of the base part 1, whereby it extends in an essentially perpendicular manner relative to the base part 1. In the vicinity of the base part 1 the stopper part 2 has a pre-shaped waist 5, i.e. a zone in which the cross-section surface of the stopper part 2 is less than in the area lying in the vicinity of the free end face 6. The free end face 6 of the stopper part 2 is preferably rounded so that the edge 7 is not sharp-edged.

With the implant represented in FIG. 1 the general shape of the base part 1 is circular and the stopper part 2 starts from the middle zone of the base part 1. Depending on the intended use of the implant, however, another form or size of the base part 1 may be desired. If no implant is available in the necessary form, the base part 1 can also be cut to size, until it has the desired shape.

If the implant or a part of it consists of a resorbable material, polydioxanone, polyglactine or a mixture of them can be used for example for this purpose.

Figure 2:
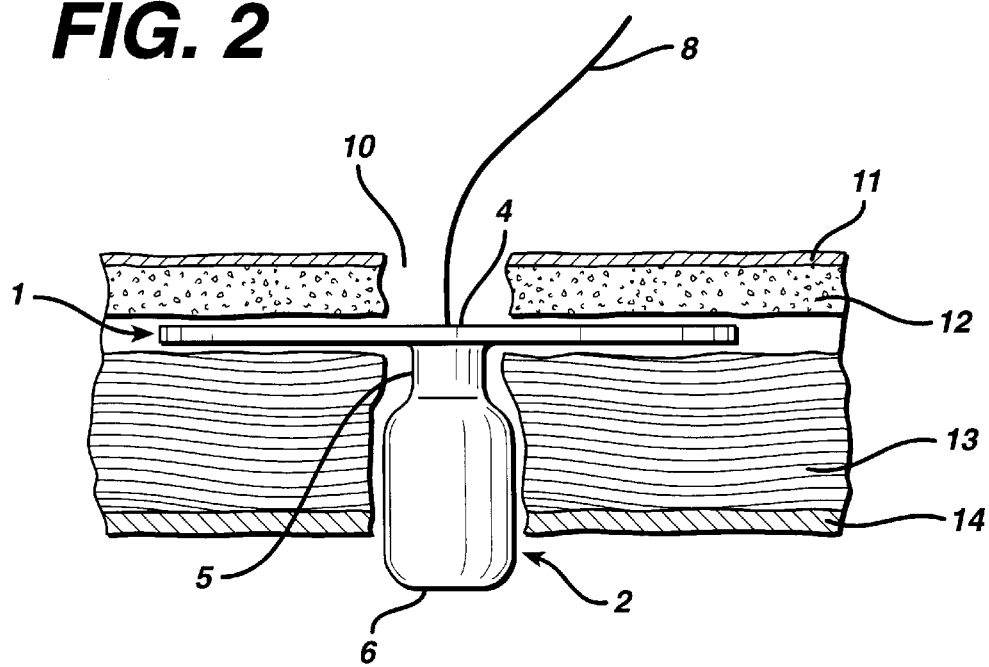
FIG. 2 a diagrammatic representation of an implant according to the invention inserted into the abdominal wall.

FIG. 2 shows an implant according to the invention after it has been inserted into a body wall in a sectional representation. As an example of a body wall, the abdominal wall is chosen, which is made up of several layers. The outermost layer is the skin (cutis) 11; below that comes the subcutaneous fatty tissue 12. Further in towards the inside of the body lie the external aponeurosis, the abdominal wall musculature and the fascia transversalis which are denoted together here with the number 13. The innermost layer is formed from the peritoneum 14.

The implant is inserted so that the free end face 6 of the stopper part 2 points to the inside of the body. The base part 1 lies between the aponeurosis (layer 13) and the subcutaneous fatty tissue 12. Attached to the side 4 of the base part 1 directed away from the stopper part 2 is a thread 8, which is not shown in FIG. 1. The thread 8 is of assistance when inserting the implant, as described below. Several threads 8 can also be provided, for example, two parallel-running threads which are joined together at their free ends. After the implant is inserted, the point where the two threads are joined together can be cut off, producing two independent threads. With the help of these threads the implant can be sewn to the skin 11 or to the aponeurosis in order to fix it even more securely.

FIG. 2 shows the preferred dimensions of the implant in relation to the tissue. The waist 5 extends over an area which corresponds approximately to the thickness of layer 13. The free end face 6 of the stopper part 2 projects slightly into the inside of the body with respect to the peritoneum 14, in order to prevent an uncontrolled ingrowth of the peritoneum 14 into the area of the penetration point. The diameter of the stopper part 2 is based on the size of the injury, that is according to the diameter of the cannula used in the operation.

The implant according to the invention can, for example, be inserted in the following way into the penetration point of a cannula. To this end, the base part 1, which is flexibly designed, is first folded up so that it points away from the free end face 6 of the stopper part 2. The entire implant can then be pushed into the cannula from the extra-corporeal end as long as the cannula is still inserted into the body wall. The free end face 6 points to the inside of the body, whilst the thread 8 has a length such that its free end remains accessible outside the body throughout the entire insertion procedure. The implant is then pushed forward, for example with the help of a rod, to the distal end of the cannula, until the free end face 6 emerges from the cannula. This procedure can be observed with the help of the usual observation instruments used in endoscopic operations. The cannula can then be withdrawn in proximal direction whilst the implant is held in its position relative to the abdominal wall with the help of the rod guided through the cannula. It should be ensured that the free end face 6 protrudes slightly vis-à-vis the peritoneum 14, as is shown in FIG. 2. If the cannula is pulled back far enough, the waist 5 rests in the area of layer 13; should the free end face 6 protrude too far into the inside of the body, the position of the implant can be corrected by pulling on thread 8. The thread 8 reliably prevents the implant being lost in the abdominal cavity. As the cannula is pulled further back, the base part 1 unfolds. The surgeon is able to place it in its desired position between the subcutaneous fatty tissue 12 and the layer 13 from the outside, for example using forceps, since both these layers can be lifted off from each other relatively easily. Finally, the implant assumes the position shown in FIG. 2. The thread 8 can then be cut off at the base part 1. Alternatively, it can be used to sew the implant securely to the aponeurosis or the cutis, as described above.

The thread 8 can be dispensed with if the implant is inserted into the cannula using a sufficiently long gripping instrument, and is held long enough until the cannula is removed and the implant has assumed its definitive position.

We claim:

1. An implant, in particular for the closure of trocar puncture points, comprising a flexible, flat base part (1) having a topside and a bottom side and a center and a stopper part (2) that extends from the bottom side (3) of the base part (1) and extends in an essentially perpendicular manner relative to the base part wherein at least one thread (8) is secure to the top side (4) and the base part (1) facing away from the stopper part (2) wherein the stopper part is fixedly mounted to the base part and has a proximal end, a distal end and a distal end face.

2. The implant according to claim 1, wherein that the stopper part (2) has a waist section (5) adjacent to the bottom side of the base part (1).

3. The implant according to claim 1, wherein the general shape of the base part (1) is circular and that the stopper part (2) extends from the center of the base part (1).

4. The implant according to claim 1, wherein the stopper part (2) is cylinder-shaped.

5. The implant according to claim 4, wherein the distal end face (6) of the stopper part (2) is rounded.

6. The implant according to claim 1, wherein the at least one thread (8) consists of resorbable material.

7. The implant according to claim 1, wherein the stopper part (2) consists of resorbable material.

8. The implant according to claim 1, wherein the base part (1) consists of resorbable material.

9. The implant according to claim 1, wherein the stopper part (2) consists of porous material.

10. The implant according to claim 1, wherein the base part (1) consists of porous material.

11. A method of closing trocar puncture points, said method comprising the steps of:

providing an implant, said implant comprising a flexible flat base part having a top side, a bottom side and a center and a stopper part that extends from the bottom sde of the base part in an essentially perpendicular manner relative to the base part;

folding the implant and inserting it into a trocar cannula;

inserting the cannula into a trocar wound extending through a peritoneum, said wound surrounded in part by a layer of subcutaneous fatty tissue;

pushing the implant through the cannula such that the distal end of the stopper part protrudes through the peritoneum and the base part unfolds to a flat configuration in the subcutaneous fatty tissue, thereby closing the trocar wound.

* * * * *

UNITED STATES PATENT AND TRADEMARK OFFICE
CERTIFICATE OF CORRECTION

PATENT NO. : 5,827,325
DATED : October 27, 1998
INVENTOR(S) : Susanne Landgrebe and Wieland Knopf It is certified that error appears in the above-indentified patent and that said Letters Patent is hereby corrected as shown below:

On the title page, item [54] and column 1, line 1

TITLE: Should Be: IMPLANT IN PARTICULAR FOR THE CLOSURE OF TROCAR PUNCTURE POINTS Claim 1
Column 4, Line 65: "sde" should be "side"

Signed and Sealed this

Ninth Day of March, 1999

*Attest:*

Q. TODD DICKINSON

*Attesting Officer*  *Acting Commissioner of Patents and Trademarks*